US005770368A

United States Patent [19]

De Leon et al.

[11] Patent Number: 5,770,368
[45] Date of Patent: Jun. 23, 1998

[54] CRYPTOSPORIDIUM DETECTION METHOD

[75] Inventors: Ricardo De Leon, Irvine; Paul A. Rochelle, Manhattan Beach, both of Calif.

[73] Assignee: Metropolitan Water District of Southern California, Los Angeles, Calif.

[21] Appl. No.: 647,351

[22] Filed: May 9, 1996

[51] Int. Cl.$^6$ .................................................... C12Q 1/68
[52] U.S. Cl. ................................ 435/6; 435/29; 435/34; 435/912
[58] Field of Search ................................. 435/6, 32, 29, 435/34, 205, 7, 91, 91.2; 536/24.3

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91.2 |
| 4,801,530 | 1/1989 | Noguiera et al. | 435/6 |
| 4,908,308 | 3/1990 | Van der Ploeg et al. | 435/6 |
| 4,957,858 | 9/1990 | Chu et al. | 435/6 |
| 4,965,188 | 10/1990 | Mullis et al. | 435/6 |
| 4,983,511 | 1/1991 | Geiger et al. | 435/6 |
| 5,004,682 | 4/1991 | Roberts et al. | 435/6 |
| 5,250,411 | 10/1993 | Ayyanathan et al. | 435/6 |
| 5,298,392 | 3/1994 | Atlas et al. . | |
| 5,409,818 | 4/1995 | Davey et al. | 435/91.21 |
| 5,437,990 | 8/1995 | Burg et al. | 435/91.2 |

FOREIGN PATENT DOCUMENTS

| | | |
|---|---|---|
| WO8909835 | 10/1989 | WIPO . |
| WO9006995 | 6/1990 | WIPO . |

OTHER PUBLICATIONS

Sheppard et al. Molecular and Biochemical Parsitology 33, 101–104, 1989.

Kumar et al. PNAS 85, pp. 6277–6281, 1988.

Eddy et al. The Journal of Biological Chemistry vol. 268 (31), pp. 23267–23274, 1993.

Haus et al. The EMBO Journal vol. 12(10), pp. 3763–3771, 1993.

Aggarwal et al. Nucleic Acids Research, vol. 18(11) p. 3409, 1990.

Abbaszadegan, M., Huber, M.S., Pepper, I.L. & Gerba, C.P., "Detection of viable Giardia cysts in water samples using polymerase chain reaction," Proceedings American Water Works Association, Water Quality Technology Conference, Toronto (1993).

Awad–El–Kariem, F.M., Warhurst, D.C. & McDonald, V., "Detection and species identification of *Cryptosporidium* oocysts using a system based on PCR and endonuclease restriction," *Transactions of the Royal Society of Tropical Medicine and Hygiene* 88:19–22 (1994).

Cai et al., "PCR cloning and nucleotide sequence determination of the 18s rRNA genes and internal transcribed spacer 1 of the protozoan parasite *Cryptosporidium parvum* and *Cryptosporidium muris,*" *Biochim. Biophys. Acta* 1131:317–320 (1992).

Chrisp et al., "Similarities and differences between DNA of *Cryptosporidum parvum* and *C. wrairi* detected by the polymerase chain reaction," *Folia Parasitol.* 41:97–100 (1994).

DuPont, H.L., Chappell, C.L., Sterling, C.R., Okhuysen, P.C., Rose, J.B. & Jakubowski, W, "The infectivity of *Cryptosporidium parvum* in healthy volunteers," *New England of Medicine* Mar. 30, 332(13):855–9 (1995).

Favennec, L., Chochillon, C., Meillet, D., Magne, D., Savel, J., Raichvarg, D. & Gobert, J.G., "Adherence and multiplication of Giardia intestinalis on human enterocyte–like differentiated (CaCo–2) cells in vitro," *Parasitology Research* 76:581–4 (1990).

Filkorn, R., Wiedenmann, A. & Botzenhart, K., "Selective detection of viable *Cryptosporidium* oocysts by PCR," *Zentralblatt Hyg. & Umweltmed* 195:489–494 (1994).

Gooze et al., Amplification of a *Cryptosporidium parvum* gene fragment encoding thymidylate synthase, *J. Protozool* 38:56s–58s (1991).

Gupta et al., "Cloning of *Giardia lamblia* heat shock protein HSP 70 homologs: implications regarding origin of eukaryotic cells and of endoplasmic reticulum," *Proc. Natl. Acad. Sci. USA* 91:2895–2899 (1994).

Johnson, D.W., Pieniazek, N.J., Griffin, D.W., Misener, L. & Rose, J.B., Development of a PCR protocol for sensitive detection of *Cryptosporidium* oocysts in water samples, *Applied and Environmental Microbiology* Nov. 61(11): 3849–55 (1995).

Khramtsov, N.V., Tilley, M., Blunt, D.S., Monteleone, B.A. & Upton, S.J., "Cloning and Analysis of a *Cryptosporidium parvum* protein with homology to cytoplasmic form HSP 70," *Journal of Eukaryotic Microbiology* 42:416–422 (1995).

(List continued on next page.)

*Primary Examiner*—James Ketter
*Assistant Examiner*—Irem Yucel
*Attorney, Agent, or Firm*—Margaret A. Churchill; David A. Farah; Sheldon & Mak

[57] ABSTRACT

The subject invention provides processes and kits for detecting encysted forms of protozoa, particularly Cryptosporidium and Giardia, that are viable and infectious. To determine viability, cysts or oocysts are heated to a temperature that induces transcription of heat shock protein (HSP) genes. Alternatively, to determine infectivity the encysted forms are inoculated onto susceptible cell cultures. The viability or infectivity of the encysted forms can be determined by synthesizing a cDNA from an induced HSP RNA template using a primer that is specific for particular genus or species of protozoa, followed by enzymatic amplification of the cDNA. Alternatively, infectivity can be determined by amplifying HSP DNA from infected cells using a primer pair that is specific for a particular genus or species of protozoa. Amplified HSP DNA can be detected using probes that are specific for a protozoan species of interest, such as the human pathogens *C. parvum* and *G. lamblia*. Moreover, both Cryptosporidium and Giardia can be detected simultaneously by using two primer pairs in a multiplex amplification reaction.

26 Claims, 3 Drawing Sheets

OTHER PUBLICATIONS

Laxer, M.A., Timblin, B.K. & Patel, R.J., "DNA sequences for the specific detection of *Cryptosporidium parvum* by the polymerase chain reaction," *American Journal of Tropical Medicine and Hygiene* 45:688–694 (1991).

LeChevallier, M.W., Norton, W.D. & Lee, R.G., "Giardia and *Cryptosporidium spp.* in filtered drinking water supplies," *Applied and Environmental Microbiology* Sep. 57(9):2617–21 (1991).

Leng, X., Mosier, D.A. & Oberst, R.D., "Simplified method for recovery and PCR detection of Cryptosporidium DNA from bovine feces," *Appl. Environ. Microbiol.* 62:643–647.

Mahbubani, M.H., Bej, A.K., Perlin, M., Schaefer, F.W., Jakubowski, W. & Atlas, R.M., "Detection of *Giardia cysts* by using the polymerase chain reaction and distinguishing live from dead cysts," *Applied and Environmental Microbiology* 57:3456–3461 (1991).

MacKenzie, W.R., Hoxie, N.J., Proctor, M.E. Gradus, M.S., Blair, K.A., Peterson, D.E., Kazmierczak, J.J., Addiss, D.G., Fox, K.R., Rose, J.B. et al., A massive outbreak in Milwaukee of cryptosporidium infection transmitted through the public water supply [published erratum appears in *New England Jounal of Medicine* Oct. 13, 331(15):1035 (1994)]; *New England Journal of Medicine* Jul. 21, 331(3):161–7 (1994).

Maresca, B. and Carratu, L., "The biology of the heat shock response in parasites," *Parasitology Today* 8:260–266.

Rose, J.B., Gerba, C.P. & Jakubowski, W., *Enviromental Science and Technology* 25:1393–1400 (1991).

Taghi–Kilani et al., "Three tandemly repeated 5s ribosomal RNA–encoding genes identified, cloned, and characterized from *Cryptosporidium parvum,"Gene* 142:253–258 (1994).

Upton, S.J., Tilley, M. & Brillhart, D.B., "Comparative development of *Cryptosporidium parvum* (Apicomplexa) in 11 continuous host cell lines," *FEMS Microbiology Letters* 118: 233–236 (1994).

Wagner–Weining, C. and Kimming, P., "Detection of viable *Cryptosporidium parvum* oocysts by PCR," *Appl. Environ. Microbiol.* 61:4514–4516 (1995).

Webster, K.A., Pow, J.D.E., Giles, M., Catchpole, J. & Woodward, M.J., "Detection of *Cryptosporidium parvum* using a specific polymrase chain reaction," *Veterinary Parasitology* 50:35–44 (1993).

Weiss, J.B., "PCR Detection of *Giardia lamblia,*" pp. 480–485 (1993). In: D.H. Pershing, T.F. Smith, F.C. Tenover & T.J. White (eds.), *Diagnostic Molecular Microbiology: Principles and Applications,*.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3607 base pairs
        ( B ) TYPE: nucleic acid
        ( C ) STRANDEDNESS: double stranded
        ( D ) TOPOLOGY: linear     ( i i ) MOLECULE TYPE: genomic DNA     ( i x ) SEQUENCE DESCRIPTION: SEQ ID NO:1:

```
GAATTCTCAT   TCTATGGTGA   AAGGTATATA   TTATAAAATT   TGTAATATTA   TAATAAAATA        60

TTTTTTTCCT   ATGAAATTTA   ATTTTACAAG   CATTAGTTTC   ATAATATAAT   CATATTGTTG       120

ATTAGTCTGT   AAAAATATTA   TTTGATTGAT   GAGGAGATCC   ATATTCACTT   TATTTTATTA       180

GAATTTTTAT   TAAATAAAAG   TTGTATTATT   TTTTTTTTAT   TGTAATTATT   AAAAATAATG       240
```

-continued

```
GCCTTTTTTT TTAATTAATA GAAATATTAT GTAGTGAATT ACAATCACAA CTTGATTTTA      300

CCATTTTATT ATATTTTTTT TAAAAATTAT TGTAATTATT TAATACTTTA CACACGTAAT      360

TTATTTTCTT CTATTGAATT AATTAAACTT TATTCCTATA ACATTCATAT ACAGTTGCAT      420

TGCAAATTTT GCATGCAATG CATGCATCAA TGTGGACAAA TTTTAATAAC GAAGCATGAA      480

CAACAACATG GCGGTTAGCT GCTAAAGTCA ATATTTACA TTAATTATTA TTATAAGAAA      540

ACGAGGAGTT GATTTATTCG GAAAGTAAAG TGATAAAGT AAATGGAAAA AAGGGAGAAA      600

ATGAGGAATA AGAGGGGGAA GAAATGAAAG AAGAAAAAT ATAAGAGAAA GAATGGGAAG      660

AGTAGTAGTA GGAAGAAGGA ACAATGTAG TGGGAAATAT AACGCAATAA AAAAAAATGG      720

ACGCTACATG AGGGAAGTTT GAAATAGTTG ATAATTAAAA ATTTTAATTT AAGTACAATT      780

TTTAATTCGA TTTCAATCTA CAAATACTAA TTAGAGAAAA TTATATGCAA TATTTTTTTT      840

CCATGTTATA GAAAATTGAA GGGTTTAGGC GCCAAATCGA GAGTTACTAC TTTGTATAAA      900

ATAATTTATA TATTAATTGC GCATTAAATA AAAATTAGGG GGTTTGGCGG TAATTCTGAG      960

ACGCAATAAT ATTTAAAATA ATAATAAATA ATCAAATATT ATAAGAAAAT GTAAATATAA     1020

TAAATGATGA AGAATAATGG TCAGTTGTTA AGTACGTATA AAATGGCAAA TACTAATCAA     1080

AATGTAAAAA ATAAATAGTA TAATGTCAAA TTATGAATAA GAAATAATAG ACACAGCTAT     1140

TTATGAGGGG AAAAGTCAAT GTGTCTCGTA AAGATTGAAA ATAAGTACA AGTTATTTA      1200

TCTCACTAGA TAAATAGTTT ATTTCATTTT AACTGATTTA ATAAATTCTT ATCGAAATTC     1260

AAAAAAACAA G ATG ACA TCA TCT GAA GGT CCA GCT ATT GGT ATT GAT TTA     1310
             Met Thr Ser Ser Glu Gly Pro Ala Ile Gly Ile Asp Leu
              1               5                  10

GGT ACC ACA TAC TCA TGT GTT GGT GTA TGG AGA AAC GAT ACT GTA GAT       1358
Gly Thr Thr Tyr Ser Cys Val Gly Val Trp Arg Asn Asp Thr Val Asp
     15                  20                  25

ATT GTT CCA AAC GAT CAA GGT AAC CGT ACA ACA CCA TCA TAT GTA GCA       1406
Ile Val Pro Asn Asp Gln Gly Asn Arg Thr Thr Pro Ser Tyr Val Ala
 30                  35                  40                  45

TTT ACA GAA ACT GAG CGT CTT ATT GGT GAT GCA GCA AAG AAC CAA GTT       1454
Phe Thr Glu Thr Glu Arg Leu Ile Gly Asp Ala Ala Lys Asn Gln Val
                 50                  55                  60

GCT AGA AAC CCA GAA AAT ACA GTT TTT GAT GCT AAA CGT CTT ATT GGT       1502
Ala Arg Asn Pro Glu Asn Thr Val Phe Asp Ala Lys Arg Leu Ile Gly
         65                  70                  75

AGA AAG TTT GAT GAT CAG GCA GTA CAA AGT GAT ATG ACT CAC TGG CCA       1550
Arg Lys Phe Asp Asp Gln Ala Val Gln Ser Asp Met Thr His Trp Pro
             80                  85                  90

TTT AAA GTA GTT AGA GGT CCA AAG GAC AAG CCA ATC ATC AGT GTA AAC       1598
Phe Lys Val Val Arg Gly Pro Lys Asp Lys Pro Ile Ile Ser Val Asn
 95                  100                 105

TAC TTA GGT GAA AAG AAG GAA TTC CAT GCT GAA GAA ATT TCT GCT ATG       1646
Tyr Leu Gly Glu Lys Lys Glu Phe His Ala Glu Glu Ile Ser Ala Met
110                  115                 120                 125

GCT TTA CAA AAG ATG AAG GAG ATC TCT GAA GCA TAC TTG GGT CGC CAA       1694
Ala Leu Gln Lys Met Lys Glu Ile Ser Glu Ala Tyr Leu Gly Arg Gln
             130                 135                 140

ATT AAG AAC GCT GTA GTT ACT GTT CCA GCT TAT TTC AAT GAC TCA CAG       1742
Ile Lys Asn Ala Val Val Thr Val Pro Ala Tyr Phe Asn Asp Ser Gln
         145                 150                 155

CGT CAA GCA ACA AAG GAT GCA GGT GCA ATT GCT GGT TTG AAT GTA ATG       1790
Arg Gln Ala Thr Lys Asp Ala Gly Ala Ile Ala Gly Leu Asn Val Met
     160                 165                 170

AGA ATC ATT AAC GAG CCA ACT GCA GCT GCT ATT GCT TAT GGT CTT GAT       1838
Arg Ile Ile Asn Glu Pro Thr Ala Ala Ala Ile Ala Tyr Gly Leu Asp
```

-continued

|     |     |     |     |     | 175 |     |     |     |     | 180 |     |     |     |     | 185 |      |
|-----|-----|-----|-----|-----|-----|-----|-----|-----|-----|-----|-----|-----|-----|-----|-----|------|
| AAG | AAA | GGA | ACT | GGC | GAG | AGA | AAT | GTA | TTG | ACT | TTC | GAT | TTA | GGT | GGT | 1886 |
| Lys | Lys | Gly | Thr | Gly | Glu | Arg | Asn | Val | Leu | Thr | Phe | Asp | Leu | Gly | Gly |      |
| 190 |     |     |     |     | 195 |     |     |     |     | 200 |     |     |     |     | 205 |      |

| GGT | ACT | TTT | GAT | GTA | TCA | TTA | TTA | ACT | ATT | GAA | GAT | GGT | ATT | TTT | GAA | 1934 |
|-----|-----|-----|-----|-----|-----|-----|-----|-----|-----|-----|-----|-----|-----|-----|-----|------|
| Gly | Thr | Phe | Asp | Val | Ser | Leu | Leu | Thr | Ile | Glu | Asp | Gly | Ile | Phe | Glu |      |
|     |     |     |     | 210 |     |     |     |     | 215 |     |     |     |     | 220 |     |      |

| GTT | AAA | GCT | ACC | GCT | GGT | GAT | ACT | CAC | TTG | GGT | GGT | GAA | GAT | TTT | GAT | 1982 |
| Val | Lys | Ala | Thr | Ala | Gly | Asp | Thr | His | Leu | Gly | Gly | Glu | Asp | Phe | Asp |      |
|     |     |     |     | 225 |     |     |     |     | 230 |     |     |     |     | 235 |     |      |

| AAC | AGA | CTC | GTA | GAA | TTC | TGT | GTA | CAA | GAT | TTC | AAG | AGA | AAG | AAT | AGA | 2030 |
| Asn | Arg | Leu | Val | Glu | Phe | Cys | Val | Gln | Asp | Phe | Lys | Arg | Lys | Asn | Arg |      |
|     |     | 240 |     |     |     |     | 245 |     |     |     |     | 250 |     |     |     |      |

| GGT | ATG | GAT | TTA | ACC | TCA | AAT | GCT | AGA | GCT | TTA | AGA | AGA | CTC | AGA | ACT | 2078 |
| Gly | Lys | Asp | Leu | Thr | Ser | Asn | Ala | Arg | Ala | Leu | Arg | Arg | Leu | Arg | Thr |      |
|     | 255 |     |     |     |     | 260 |     |     |     |     | 265 |     |     |     |     |      |

| CAA | TGC | GAG | CGT | GCA | AAG | AGA | ACT | TTG | TCA | TCT | TCT | ACT | CAA | GCT | ACA | 2126 |
| Gln | Cys | Glu | Arg | Ala | Lys | Arg | Thr | Leu | Ser | Ser | Ser | Thr | Gln | Ala | Thr |      |
| 270 |     |     |     |     | 275 |     |     |     |     | 280 |     |     |     |     | 285 |      |

| ATT | GAG | TTA | GAT | TCA | CTC | TAT | GAA | GGT | ATT | GAT | TAT | TCA | GTT | GCC | ATC | 2174 |
| Ile | Glu | Leu | Asp | Ser | Leu | Tyr | Glu | Gly | Ile | Asp | Tyr | Ser | Val | Ala | Ile |      |
|     |     |     |     | 290 |     |     |     |     | 295 |     |     |     |     | 200 |     |      |

| AGT | AGA | GCT | AGA | TTC | GAA | GAA | CTC | TGC | GCC | GAT | TAC | TTC | CGT | GCA | ACT | 2222 |
| Ser | Arg | Ala | Arg | Phe | Glu | Glu | Leu | Cys | Ala | Asp | Tyr | Phe | Arg | Ala | Thr |      |
|     |     | 205 |     |     |     |     | 210 |     |     |     |     | 215 |     |     |     |      |

| TTA | GCT | CCA | GTT | GAG | AAA | GTA | CTC | AAG | GAT | GCT | GGT | ATG | GAC | AAG | AGA | 2270 |
| Leu | Ala | Pro | Val | Glu | Lys | Val | Leu | Lys | Asp | Ala | Gly | Met | Asp | Leu | Arg |      |
|     |     | 220 |     |     |     |     | 225 |     |     |     |     | 230 |     |     |     |      |

| TCT | GTA | CAT | GAT | GTT | GTA | TTG | GTT | GGT | GGT | TCT | ACA | CGT | ATT | CCA | AAG | 2318 |
| Ser | Val | His | Asp | Val | Val | Leu | Val | Gly | Gly | Ser | Thr | Arg | Ile | Pro | Lys |      |
|     | 235 |     |     |     |     | 240 |     |     |     |     | 245 |     |     |     |     |      |

| GTT | CAG | GCC | TTG | ATT | CAG | GAA | TTC | TTT | AAC | GGT | AAA | GAG | CCA | TGC | AAA | 2366 |
| Val | Gln | Ala | Leu | Ile | Gln | Glu | Phe | Phe | Asn | Gly | Lys | Glu | Pro | Cys | Lys |      |
| 250 |     |     |     |     | 255 |     |     |     |     | 260 |     |     |     |     | 265 |      |

| GCA | ATC | AAT | CCA | GAC | GAA | GCT | GTT | GCT | TAT | GGT | GCT | GCT | GTA | CAA | GCT | 2414 |
| Ala | Ile | Asn | Pro | Asp | Glu | Ala | Val | Ala | Tyr | Gly | Ala | Ala | Val | Gln | Ala |      |
|     |     |     |     | 270 |     |     |     |     | 275 |     |     |     |     | 280 |     |      |

| GCT | ATC | TTA | AAT | GGT | GAG | CAA | TCC | TCT | GCC | GTA | CAG | GAT | CTC | TTA | TTA | 2462 |
| Ala | Ile | Leu | Asn | Gly | Glu | Gln | Ser | Ser | Ala | Val | Gln | Asp | Leu | Leu | Leu |      |
|     |     |     | 285 |     |     |     |     | 290 |     |     |     |     | 295 |     |     |      |

| TTG | GAT | GTT | GCT | CCA | TTA | TCA | CTC | GGT | TTA | GAA | ACT | GCT | GGT | GGT | GTT | 2510 |
| Leu | Asp | Val | Ala | Pro | Leu | Ser | Leu | Gly | Leu | Glu | Thr | Ala | Gly | Gly | Val |      |
|     |     | 300 |     |     |     |     | 305 |     |     |     |     | 310 |     |     |     |      |

| ATG | ACC | AAG | CTT | ATT | GAA | CGT | AAT | ACA | ACT | ATC | CCA | GCA | AAG | AAG | ACA | 2558 |
| Met | Thr | Lys | Leu | Ile | Glu | Arg | Asn | Thr | Thr | Ile | Pro | Ala | Lys | Lys | Thr |      |
|     | 315 |     |     |     |     | 320 |     |     |     |     | 325 |     |     |     |     |      |

| CAA | GTC | TTC | ACT | ACT | TAT | GCT | GAT | AAC | CAG | AGT | GGT | GTC | TTG | ATC | CAA | 2606 |
| Gln | Val | Phe | Thr | Thr | Tyr | Ala | Asp | Asn | Gln | Ser | Gly | Val | Leu | Ile | Gln |      |
| 330 |     |     |     |     | 335 |     |     |     |     | 340 |     |     |     |     | 345 |      |

| GTT | TAT | GAG | GGT | GAG | AGA | GCC | ATG | ACT | AAG | GAT | AAC | CAT | CTC | CTC | GGA | 2654 |
| Val | Tyr | Glu | Gly | Glu | Arg | Ala | Met | Thr | Lys | Asp | Asn | His | Leu | Leu | Gly |      |
|     |     |     |     | 350 |     |     |     |     | 355 |     |     |     |     | 360 |     |      |

| AAG | TTC | CAT | CTT | GAT | GGT | ATT | CCA | CCA | GCA | CCA | AGA | GGT | GTA | CCA | CAA | 2702 |
| Lys | Phe | His | Leu | Asp | Gly | Ile | Pro | Pro | Ala | Pro | Arg | Gly | Val | Pro | Gln |      |
|     |     |     | 365 |     |     |     |     | 370 |     |     |     |     | 375 |     |     |      |

| ATT | GAA | GTC | ACC | TTT | GAT | ATT | GAT | GCT | AAT | GGT | ATC | TTG | AAT | GTG | TCT | 2750 |
| Ile | Glu | Val | Thr | Phe | Asp | Ile | Asp | Ala | Asn | Gly | Ile | Leu | Asn | Val | Ser |      |
|     |     |     | 380 |     |     |     |     | 385 |     |     |     |     | 390 |     |     |      |

| GCT | GTT | GAT | AAG | AGT | ACT | GGT | AAG | AGC | AGC | AAG | ATC | ACT | ATT | ACT | AAC | 2798 |
| Ala | Val | Asp | Lys | Ser | Thr | Gly | Lys | Ser | Ser | Lys | Ile | Thr | Ile | Thr | Asn |      |

-continued

```
                  395                            400                            405
GAT  AAG  GGT  AGA  TTA  TCA  AAG  GTA  TCT  GAT  ATT  GAA  CGT  ATG  GTT  AAT        2846
Asp  Lys  Gly  Arg  Leu  Ser  Lys  Val  Ser  Asp  Ile  Glu  Arg  Met  Val  Asn
410                      415                      420                      425

GAT  GCT  GAG  AAA  TAC  AAG  GGT  GAG  GAT  GAG  CAG  AAC  AGA  CTT  AAG  ATT        2894
Asp  Ala  Glu  Lys  Tyr  Lys  Gly  Glu  Asp  Glu  Gln  Asn  Arg  Leu  Lys  Ile
                    430                      435                      440

GAG  GCT  AAG  AAC  TCT  TTG  GAG  AAC  TAC  CTC  TAT  AAC  ATG  AGG  AAC  ACC        2942
Glu  Ala  Lys  Asn  Ser  Leu  Glu  Asn  Tyr  Leu  Tyr  Asn  Lys  Arg  Asn  Thr
               445                      450                      455

ATC  CAA  GAA  CCA  AAG  GTT  AAG  GAA  AAG  CTT  TCT  CAA  TCT  GAA  ATT  GAT        2990
Ile  Gln  Glu  Pro  Lys  Val  Lys  Glu  Lys  Leu  Ser  Gln  Ser  Glu  Ile  Asp
          460                      465                      470

GAG  GCT  GAG  AAG  AAG  ATC  AAG  GAT  GCT  CTT  GAC  TGG  CTC  GAG  CAC  AAC        3038
Glu  Ala  Glu  Lys  Lys  Ile  Lys  Asp  Ala  Leu  Asp  Trp  Leu  Glu  His  Asn
475                      480                      485

CAA  ACT  GCT  GAA  AAG  GAC  GAG  TTT  GAA  CAT  CAA  CAA  AAG  GAG  ATT  GAA        3086
Gln  Thr  Ala  Glu  Lys  Asp  Glu  Phe  Glu  His  Gln  Gln  Lys  Glu  Ile  Glu
490                      495                      500                      505

ACT  CAT  ATG  AAT  CCA  CTC  ATG  ATG  AAG  ATC  TAC  TCT  GCT  GAG  GGT  GGT        3134
Thr  His  Lys  Asn  Pro  Leu  His  Met  Lys  Ile  Tyr  Ser  Ala  Glu  Gly  Gly
                         510                      515                      520

ATG  CCA  GGT  GGA  ATG  CCA  GGT  GGT  ATG  CCA  GGC  GGT  ATG  CCA  GGT  GGA        3182
Met  Pro  Gly  Gly  Met  Pro  Gly  Gly  Met  Pro  Gly  Gly  Met  Pro  Gly  Gly
               525                      530                      535

ATG  CCA  GGT  GGT  ATG  CCA  GGT  GGA  ATG  CCA  GGC  GGT  ATG  CCA  GGT  GGT        3230
Met  Pro  Gly  Gly  Met  Pro  Gly  Gly  Met  Pro  Gly  Gly  Met  Pro  Gly  Gly
          540                      545                      550

ATG  CCA  GGT  GGT  ATG  CCA  GGT  GGT  ATG  CCA  GGA  TCT  AAT  GGT  CCA  ACT        3278
Met  Pro  Gly  Gly  Met  Pro  Gly  Gly  Met  Pro  Gly  Ser  Lys  Gly  Pro  Thr
555                      560                      565

GTT  GAA  GAG  GTC  GAC  TAATTATTTT  AGTCACCAAA  AAAACTCACT  CAAAATGGAA              3333
Val  Glu  Glu  Val  Asp
570

AGTTAAGAAC  TATTTACACA  CTTTCAATTT  CTAGTTATTT  TTTACCAAAA  TAAGAAGAAA              3393

AGCACACTCT  ACCTTTAGGC  TATATTTTCC  ATTCTCTAGC  CTAGACTCCC  TTATATGCGA              3453

GTTGGCAATA  TTTCACCAGA  TTTACCGCCA  TAAATTTGGC  ATTTTTGGCT  TATTGATAGT              3513

CATTACTATT  ATCAATACGA  GTTCTCGAAA  AGAGAAAGGC  CAGATATCTG  GATAGTTTGG              3573

AACAAACTAT  GTTCTCTAGT  TTATTTGAGA  ATTC                                            3607
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: Other nucleic acid
        ( A ) DESCRIPTION: primer sequence     ( i x ) SEQUENCE DESCRIPTION: SEQ ID NO:2:

CTGTTGCTTA TGGTGCTGCT G                            21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid
   ( A ) DESCRIPTION: primer sequence ( i x ) SEQUENCE DESCRIPTION: SEQ ID NO:3:

CCTCTTGGTG CTGGTGGAAT A                                                          21

( 2 ) INFORMATION FOR SEQ ID NO:4:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid
      ( A ) DESCRIPTION: primer sequence ( i x ) SEQUENCE DESCRIPTION: SEQ ID NO:4:

AAATGGTGAG CAATCCTCTG                                                            20

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid
      ( A ) DESCRIPTION: primer sequence ( i x ) SEQUENCE DESCRIPTION: SEQ ID NO:5:

CTTGCTGCTC TTACCAGTAC                                                            20

( 2 ) INFORMATION FOR SEQ ID NO:6:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: Other nucleic acid
      ( A ) DESCRIPTION: primer sequence ( i x ) SEQUENCE DESCRIPTION: SEQ ID NO:6:

AGGGCTCCGG CATAACTTTC C                                                          21

( 2 ) INFORMATION FOR SEQ ID NO:7:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid
      ( A ) DESCRIPTION: primer sequence ( i x ) SEQUENCE DESCRIPTION: SEQ ID NO:7:

GTATCTGTGA CCCGTCCGAG                                                            20

( 2 ) INFORMATION FOR SEQ ID NO:8:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear (  i i ) MOLECULE TYPE: Other nucleic acid
        ( A ) DESCRIPTION: probe sequence ( i x ) SEQUENCE DESCRIPTION: SEQ ID NO:8:

A A A T G G T G A G   C A A T C C T C T G   C C G                                23

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: probe sequence ( i x ) SEQUENCE DESCRIPTION: SEQ ID NO:9:

C C A T T A T C A C   T C G G T T T A G A                                        20

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: probe sequence ( i x ) SEQUENCE DESCRIPTION: SEQ ID NO:10:

C A G G C C T T G G   C G T T C C C G A A   G                                    21

CRYPTOSPORIDIUM DETECTION METHOD

BACKGROUND

Protozoan parasites are a major cause of gastrointestinal disease. Within the last decade, the protozoa Cryptosporidium and Giardia have been increasingly associated with waterborne outbreaks of acute diarrhea. *Cryptosporidium parvum* is of particular concern because no known treatment of the illness is available at present. Moreover, in the immunocompromised host a *C. parvum* infection can lead to prolonged severe diarrhea, malnutrition, wasting, and death.

Cryptosporidium is an enteric coccidia, which has a multi-staged life cycle one to eight days in duration. The oocyst contains four sporozoites which, during normal infection, are released in the presence of bile salts and proteases. The sporozoites attach and penetrate intestinal epithelial cells. Once inside they develop into a rounded trophozoite in the area between the cytoplasmic membrane and the cytoplasm. Through asexual reproduction, the trophozoite (a type I meront) forms up to eight merozoites. The merozoites may then develop into a type 11 meront, which by asexual reproduction forms four merozoites. The second generation merozoites may develop into male (microgamont) or female (macrogamont) forms. The male form may lead to the sexual phase of the Cryptosporidium life cycle which culminates, in vivo, in the production of the environmentally resistant oocysts. These hardy structures possess a thick, double-layered protective cell wall which is resistant to most disinfectants, chlorine concentrations generally present in municipal water supplies, and temperatures between $-4°$ C. and $60°$ C.

Cryptosporidium is prevalent in most vertebrate groups. Domestic animals, such as rodents, kittens, puppies, and calves may constitute an important reservoir of the human Cryptosporidium. However, disease outbreaks in day-care centers, hospitals and urban family groups indicate that most human infections are transmitted person-to-person rather than via a zoonotic route. Since oocysts are found almost exclusively in stool, the transmission is undoubtedly fecal-oral. Moreover, the recovery of oocysts from both surface and drinking water suggests that indirect transmission via water is not uncommon.

Quantitative studies on the infectious dose for humans are currently limited. One study found that, in healthy volunteers, the infectious dose ($ID_{50}$) is 132 oocysts, with as few as 30 oocysts causing infection in 20% of individuals tested (DuPont et al., 1995). However, the $ID_{50}$ could be lower, e.g. one to ten oocysts, in more susceptible individuals.

Indeed, Cryptosporidium has been documented as a major cause of waterborne illness on numerous occasions. The largest outbreak occurred during the spring of 1993, in Milwaukee, Wis., resulting in approximately 400,000 illnesses and 100 deaths (MacKenzie et al., 1994).

Cryptosporidium has been found to be somewhat ubiquitous in source waters. Two large multi-state surveys found Cryptosporidium in 50% of source waters tested (LeChevalier et al, 1991, and Rose et al., 1991). The Metropolitan Water District of Southern California (MWD) found Cryptosporidium in 24% of source water samples tested (unpublished data, 1992). Cryptosporidium was also found in 27%, 17%, and 6% of finished water samples in the LeChevalier, Rose, and MWD surveys, respectively.

These studies, surveys, and documented outbreaks clearly indicate that infectious Cryptosporidium may be found in source water and the efficiency of conventional water treatment needs to be closely monitored. Indeed, the occurrence of the causative agents *Cryptosporidium parvum* and *Giardia lamblia* in water supplies has become a critical issue for the water industry.

The current techniques for isolating Cryptosporidium and Giardia from water involve filtration and centrifugation to concentrate and purify oocysts and cysts, respectively, followed by immunofluorescence microscopy. Objects with the correct shape, dimensions, and fluorescence are confirmed by observation of internal structures using differential interference contrast microscopy. The limitations of these procedures includes loss of oocysts or cysts during isolation, resulting in recovery efficiencies ranging from 70 to 80 percent to less than one percent for Cryptosporidium. Moreover, the immunofluorescent assay (IFA) method cannot distinguish viable and potentially infective from non-viable or non-infective oocysts and cysts. Additional limitations of IFA include nonspecific antibody binding and cross-reactive antibody binding among human and animal infective species of Cryptosporidium or Giardia.

For the foregoing reasons, there is a need for an alternative method of detecting Cryptosporidium and Giardia pathogens that is rapid, sensitive, and specific. Ideally the method can distinguish among human and animal infective Cryptosporidium and/or Giardia species. Moreover, the alternative method should be able to determine if Cryptosporidium oocysts and/or Giardia cysts are viable and infective.

SUMMARY

The present invention is directed to detection methods and kits that satisfy these needs. Detection of viable and infective protozoa, particularly encysted forms of Cryptosporidium and Giardia, is accomplished by the enzymatic amplification of a target gene sequence, which encodes an inducible heat shock protein (HSP). The method exploits the speed, sensitivity, and specificity associated with an amplification procedure, such as polymerase chain reaction (PCR). Pathogenic forms of protozoa present in low copy numbers can be identified and distinguished from morphologically similar but non-pathogenic protozoa.

A first version of the invention is a method that selectively detects viable protozoan oocysts from a test sample. Oocysts are recovered from the test sample and the temperature is elevated to induce the transcription of heat shock protein (HSP) RNA. The oocysts are then lysed to release the RNA and DNA is removed from the lysate. A single-stranded cDNA is synthesized that is complementary to the HSP RNA by combining the RNA, a DNA polymerase having reverse transcriptase activity, four different deoxynucleotide triphosphates, and a first primer, which is complementary to a target HSP RNA sequence. A double-stranded cDNA sequence is then synthesized by incubating the single-stranded cDNA from the preceding step with a DNA polymerase, four different deoxynucleotide triphosphates, and a second primer. The second primer is complementary to a portion of the single-stranded cDNA and can initiate synthesis of a second cDNA strand. The double-stranded cDNA is then amplified to form an amplified target DNA by one of the amplification procedures well known in the art, such as PCR. The presence of viable oocysts is then determined by detecting the amplified target DNA.

A second version of the invention is a method that selectively detects infective protozoan oocysts in a sample. Cell cultures, which are susceptible to infection, are inoculated with a sample suspected of harboring infective oocysts. The cell culture is incubated under conditions that permit the infective oocysts to infect the susceptible cells. Cultured cells are then treated to gain access to the nucleic acids within the cells. An HSP gene sequence is selected as a target for detection. The nucleic acids from the cells serve as templates for at least two rounds of DNA synthesis, where a first primer and then a second primer hybridize with a portion of a first strand and a second strand of the HSP gene sequence. The primers initiate synthesis of a double-stranded polynucleotide sequence which is subsequently amplified by an appropriate amplification procedure. The presence of infective oocysts is then determined by detecting the amplified target DNA.

The second version of the invention may amplify either DNA or RNA from the infected cells. Moreover, a quantitative assay for infective oocysts can be performed by adjusting, if necessary, the amount of oocysts used to inoculate the cells to a level that permits the enumeration of infection foci. Formation of discrete infection foci can be facilitated by adding an overlay to the cell culture, which retards the migration of infective organisms.

The invention can be adapted to detect HSP sequences conserved among different members of Cryptosporidium genus. In addition, the invention can be adapted to only detect the human pathogen, C. parvum. A third alternative is to simultaneously detect Cryptosporidium and Giardia. The specificity of the method is determined by the choice of primer pairs that specifically recognize HSP sequences for the protozoa of interest. In addition, the identification of a protozoa of interest can be confirmed by using oligonucleotide probes, which can hybridize with the amplified HSP target DNA.

The invention also provides kits for use in amplifying and detecting viable or infective Cryptosporidium and/or Giardia organisms. The kits can contain suitable amounts of the primers, or a suitable amount of the probe, or suitable amounts of the primers and probe.

DRAWINGS

These and other features, aspects, and advantages of the present invention will become better understood with regard to the following description, appended claims and accompanying drawings where:

FIG. 2A shows amplification of DNA from C. parvum (lanes 1–5) and C. muris (lanes 6–10) by PCR using primer pair SEQ ID NO: 2 and SEQ ID NO: 3, which amplifies Cryptosporidium heat shock protein gene (HSP70) to give a 307 bp product (lanes 1 and 6), primer pair SEQ ID NO: 4 and SEQ ID NO: 5, which amplifies the C. parvum HSP70 gene to give a 361 bp product (lanes 2 and 7), primer pair LAX469F and LAX869R, which amplifies an undefined genomic region of Cryptosporidium DNA to give a 451 bp product (lanes 3 and 8), primer pair AWA722F and AWA1325R, which amplifies a portion of a Cryptosporidium 18S rRNA gene to give 556 bp product (lanes 4 and 9), and primer pair AWA 995F and AWA1206R, which amplifies another portion of a Cryptosporidium 18S rRNA gene to give a 256 bp product (lanes 5 and 10); Lane 11 contained a molecular weight marker.

DETAILED DESCRIPTION

I. OVERVIEW

The present invention provides a method for amplifying and detecting viable and/or infective Cryptosporidium oocysts by monitoring the presence or absence of heat shock protein (HSP) genes and their transcripts. The heat shock response has a fundamental role during host invasion by parasites. When parasitic microorganisms infect another organism they experience an increase in environmental temperature, because the body temperature of the host organism is higher than that of the surrounding environment. The physiological response of cells or entire organisms to this increased temperature is called the heat shock response and is characterized by increased transcription of the HSP genes (Maresca and Carratu, 1992). Increased expression (determined by elevated concentrations of mRNA) of HSP genes has been detected in a range of organisms including Plasmodium, Trypanosoma, Candida, and Giardia (Maresca and Carratu, 1992).

Since HSP gene transcription is a physiological response of living cells to an environmental stimulus, only viable Cryptosporidia are identified by amplifying and detecting HSP RNA transcripts from intact oocysts. Alternatively, infective Cryptosporidia are determined by first inoculating susceptible cell cultures with oocysts, and subsequently amplifying and detecting HSP DNA or RNA molecules from infected cells. A third alternative provides a method for simultaneously detecting Cryptosporidium and Giardia HSP gene amplification products.

II. RECOVERY OF OOCYSTS

The diagnosis of Cryptosporidium and Giardia is generally established by the recovery of Cryptosporidium oocysts and Giardia cysts from stool specimens. Alternatively, evidence for indirect transmission via contaminated water is provided by concentrating Cryptosporidium oocysts and Giardia cysts from water samples.

Cryptosporidium oocysts and Giardia cysts can be concentrated from water by a variety of methods. For example, a predetermined volume of water, e.g. 100 liters, can be filtered through a 1 $\mu$m nominal porosity yarn-wound polypropylene filter or its equivalent. The filtration flow rate is restricted to about 4 liters/min. Sampled filters are typically shipped on ice to analytical laboratories for analysis within 24 hours. Retained protozoa are eluted from the filter within 96 hours of collection with a buffered detergent solution, filter fibers are cut, teased and washed by hand or with the aid of a stomacher. Oocysts or cysts recovered in the eluent are concentrated by centrifugation and partially purified by flotation on a Percoll-sucrose solution with a specific gravity of 1.1. A portion of the purified material is placed on a membrane filter, tagged with antibody using the indirect staining method, and examined under UV microscopy. Specific criteria are used to identify cysts and oocysts including, immunofluorescence, size, shape, and internal morphology.

III. INFECTIVITY ASSAY

To determine infectivity, oocysts are inoculated onto susceptible cells, incubated under conditions that permit infection of cells to occur, and tested for the presence of HSP target DNA or RNA by an amplification procedure. Prior to the inoculation step the oocysts are decontaminated and, optionally, subjected to an excystation protocol.

A. OOCYST PRE-TREATMENT

Oocysts recovered from water samples and stool specimens should be decontaminated to kill other microorganisms that may be present in the sample. Oocysts can be decontaminated by treatment with 10% chlorine bleach followed by washing with sterile 0.1% sodium thiosulfate to remove residual chlorine. If necessary, oocysts can also be treated with antibiotics prior to inoculation.

An optional excystation procedure may be included in oocyst pre-treatments to release sporozoites and improve infectivity. For example, oocysts are pelleted for 2 min at 5,000 x g in a microfuge, resuspended with ice-cold 10% chlorine bleach solution, and allowed to stand for 10 min on ice. The oocysts are then washed twice by successive pelleting and resuspension in sterile ice-cold saline solution. Finally, the decontaminated oocysts are resuspended in 1 ml of cell culture growth media.

An alternative excystation procedure includes the following steps. Purified oocysts are suspended in PBS and placed on ice. An equal volume of cold 40% chlorox bleach solution is added to the oocyst suspension and the mixture is allowed to stand on ice for 1 min. Oocysts are washed 2—3 times in cold phosphate buffered saline (PBS) to remove the bleach and pre-incubated in PBS for 1 hr at 37° C. An equal volume of prewarmed excystation fluid, consisting of 0.25% trypsin and 0.75% taurocholic acid, is added to the oocysts. The oocysts are incubated for up to 2 hrs at 37° C. on a shaker.

When excystation is complete, excysted sporozoites are recovered by filtration through a syringe filter with a pore size of about 0.2 μm. Sporozoites are washed in Hanks Balanced Salt Solution (HBSS) to remove the excystation fluid.

B. INOCULATION

Cryptosporidium oocysts or sporozoites are inoculated onto susceptible cells to determine whether the oocysts or sporozoites are capable of initiating an infection. Cells that are susceptible to Cryptosporidium infection include CaCo-2, HCT-8, and MDBK cells (ATCC Numbers HTB-37, CCL 244, and CCL-22, respectively). See also, Upton et al., 1994; Favennec et al., 1990. Susceptible cells can be grown as monolayers. When the monolayers are 90% confluent, an inoculum is placed on the cells in a volume that is sufficient to cover the monolayer. The cells are then incubated at 37° C. for 2 hours in 5% $CO_2$, 95% air. Inoculated monolayers are washed once with a saline-antibiotics solution to remove residual toxicity and re-incubated at 37° C.

Inoculation of Giardia cysts can be conducted similarly to Cryptosporidium infection. Excystation and decontaminating conditions are optimized for Giardia when Roswell Park Memorial Institute (RPMI) media supplemented with L-cysteine is used to stabilize cyst and trophozoite viability. The supernatant as well as the cell monolayer can be tested to determine if adequate numbers of Giardia trophozoites have attached to cell monolayers.

C. QUANTITATIVE INFECTIVITY ASSAY

A quantitative infectivity assay can be performed by preparing cell monolayers attached to microscope slides and inoculating the cell with a measured dose of inoculum. Preferably, the slides are pre-treated with silane, collagen, BSA, laminin, fibronectin, or other cell attachment factors to increase cell adherence. Oocyst preparations are serially diluted until the inoculum contains less than about 1 oocyst per cell, i.e, a multiplicity of infection less than one (MOI<1).

Quantitative accuracy may be affected if mobile sporozoites and stage I or II merozoites are able to produce secondary infection sites. Short incubation periods, e.g., 24 hrs, may prevent some mobility of organisms. However, the movement of parasites is preferably restricted by the use of overlays. For example, soft agarose, agar, and methylcellulose overlays can be used to restrict movement of parasites only to adjacent cells (cell-to-cell transmission). As a result, discrete infection foci are produced, which can be enumerated.

D. FIXATION TREATMENTS

Subsequent cDNA synthesis, amplification, and detection procedures can occur in situ, i.e. within the confines of infected cells. Accordingly, the cells are fixed, in a manner that does not destroy cell morphology. An optimum fixation procedure will permit the reagents for subsequent reactions to diffuse into the semi-permeabilized cell. In addition, the reaction products should not be able to diffuse out of the semi-permeabilized cells.

A preferred fixation method includes treating the slides with methanol:acetic acid (3:1) at room temperature for 5 min. Following acidic methanol fixation, cells are rehydrated in graded ethanol (95%, 70%, and 50%, 2 min each) and treated with 200 μl proteinase K (5 μg/ml) for 15 min at 37° C. in a humid chamber. After the proteinase treatment, the slides are rinsed in PBS, pH 7.4 for 5 min. at room temperature. If the cells are to be used for detecting RNA, then 200 μl of an RNase-free DNase solution (about 750 U/ml) is layered on the cells, covered with a cover slip, and incubated in a humid chamber for about two to about four hours at room temperature. Alternatively, if only DNA is to be detected, the cells are treated in a similar manner with DNase-free RNase A. Following nuclease treatment, the cultured cells are washed with PBS and dehydrated in graded ethanol (50%, 70%, 95%, and 100%, 2 min each)

IV. PREPARATION OF NUCLEIC ACID EXTRACTS

Subsequent cDNA synthesis and amplification procedures can also be performed using nucleic acid containing extracts from cysts, oocysts, and infected cell cultures. Nucleic acids can be liberated from cysts, oocysts, and infected cell cultures by any method capable of lysing the cells. For example, the oocysts can be frozen in liquid nitrogen for 2 min., followed by thawing at 95° C. for 5 min. The freeze/thaw cycle can be repeated, if necessary, and the lysate can be used directly in an amplification reaction.

If the extracts are to be used for detecting DNA, RNA can be removed from the lysate by treatment with DNase-free RNase A. Further purification of DNA from oocysts and infected cell cultures can be accomplished by additional extraction steps. For example, cells can be lysed in 50 mM Tris-HCl, 20 mM EDTA, pH 8, containing 2 mg/ml proteinase K and 0.5% sarkosyl, and incubated at 37° C. for 1 h. Then, 5M NaCl is added to give a final concentration of 1M, and CTAB (hexadecyltrimethyl ammonium bromide) is added to a concentration of 1%. Following incubation at 65° C. for 30 min, the lysate is subjected to at least one freeze/thaw cycle, and phenol/chloroform extraction. The DNA is precipitated by the addition of 0.6 vol, of isopropanol and the DNA precipitate is then washed with 70% ethanol.

If the extracts are to be used for detecting RNA, then DNA can be removed from the lysate by treatment with RNase-free DNase. Total RNA can be also be isolated from lysed cells by extraction with strong denaturants, such as guanidium thiocyanate, followed by centrifugation through a cesium chloride solution. Moreover, mRNA can be isolated using solid state particles attached to oligo-dT, which can select mRNA transcripts having a poly(A) tail.

V. SYNTHESIS OF cDNA

Expression of mRNA from HSP genes can be induced by incubating cysts, oocysts, or infected cells at about 37° C. to about 42° C. for 30 min. A cDNA, complementary to the HSP mRNA, can then be synthesized by a reverse transcription reaction. The basic components for synthesizing a first strand of cDNA includes an HSP RNA template, a DNA polymerase having reverse transcriptase activity, sufficient amounts of four different nucleotide triphosphates, e.g. dATP, dCTP, dGTP, dUTP, or their analogs, and a first primer. The target HSP RNA template can be extracted from lysed cysts, oocysts, or infected cells. Alternatively the HSP RNA can remain within fixed cells for an in situ reaction. Moreover, the first primer can hybridize with a portion of the HSP mRNA, thereby initiating the synthesis of the first cDNA.

The reverse transcriptase reactions typically contain: 10 mM Tris-HCl, pH 8.3, 50 mM KCl, 2–5 mM $MgCl_2$, 1 mM each dATP, dCTP, dGTP, dUTP, 1 U/$\mu$l RNase inhibitor, 2.5 U/$\mu$l reverse transcriptase, 0.5 $\mu$M specific primer or 2.5 $\mu$M random primers, and total RNA or messenger RNA from at least one oocyst, in a 20 $\mu$l reaction. The reaction mixture can be incubated within a test tube or a multiwell plate. Alternatively, an in situ reaction is conducted by layering the mixture directly onto cells, placing a coverslip on top of the mixture, and sealing the edges of the coverslip with rubber cement or other suitable sealant. The reaction is preferably performed at 42° C. for 15–60 min followed by 5 min at 99° C. to stop the reaction.

VI. AMPLIFICATION

The amplification step of the present invention can be conducted using any of the amplification systems known in the art including the polymerase chain reaction system (U.S. Pat. Nos. 4,683,195; 4,683,202; and 4,965,188), the ligase amplification system (PCT Patent Publication No. 89/09835) the self-sustained sequence replication system (U.S. Pat. No. 5,409,818 and PCT Patent Publication No. 90/06995), the transcription-based amplification system (U.S. Pat. No. 5,437,990), and the Q$\beta$ replicase system (U.S. Pat. No. 4,957,858). Each of the foregoing patents and publications is incorporated herein by reference.

A. POLYMERASE CHAIN REACTION

PCR is the preferred amplification system of the present invention. In the PCR amplification procedure a target HSP nucleic acid sequence is amplified by treating the double-stranded polynucleotide with two oligonucleotide primers, each being complementary to one of the two strands. The primers hybridize with their complementary stands and extension products are synthesized using DNA polymerase and four different deoxynucleotide triphosphates. The DNA polymerase is preferably a thermostable enzyme, such as Taq, Tth, Pfu, or any other native, mutated, or deleted enzyme derived from a thermophilic organism. The extension products are separated from their complementary strands by denaturation at an elevated temperature, generally from about 80° to 100° C. The reaction mixture is repeatedly cycled between a low temperature annealing step, generally of from about 37° to 70° C., an intermediate temperature primer extension step, generally of from about 70° to 80° C., and a higher temperature denaturation step, generally of from about 80° to 100° C. If a thermostable DNA polymerase is used, the polymerase reaction can be cycled many times, typically 20–40 times, without needing additional enzyme.

B. IN SITU AMPLIFICATION

Reagent mixtures and conditions for in situ amplification are generally the same as those for standard PCR although concentrations of $MgCl_2$ and thermostable DNA polymerase are generally higher. Cycling parameters are determined by the optimal annealing temperature of the primers and the length of the PCR amplification product. Reaction sensitivity and specificity can be improved by using a "hot start", which prevents mis-priming and non-specific amplification. A hot start can be achieved by adding Taq polymerase only after the amplification reagents have reached 55° C. However, chemical hot start methods, e.g. by inclusion of dUTP and uracil-DNA glycosylase (UDG) or Taq antibodies (TaqStart™ Clontech), both of which inhibit PCR below 50° C., are preferred for in situ PCR due to their relative convenience.

For a typical in situ PCR, slides are heated to about 80° C. and about 30 $\mu$l of preheated (80° C.) amplification cocktail is layered onto the fixed cells. A coverslip is placed on top of the reaction mixture and the edges are sealed with rubber cement. A typical amplification cocktail contains: 10 mM Tris-HCl, pH 8.3; 50 mM KCl; about 2 mM to about 5 mM $MgCl_2$; about 250 $\mu$m each of dATP, dCTP, dGTP, and dUTP; about 3 $\mu$g/ml BSA; 10% glycerol; about 0.5 $\mu$M of each primer; and about 5 U to about 10 U of thermostable polymerase. Although other deoxynucleotide triphosphates may be included, dUTP is a preferred reaction component because UDG can be used to prevent carryover contamination of amplification reactions and as a chemical hot start. Temperature cycling can be performed in a dedicated in situ PCR thermal cycler (PTC-100-16MS, M.J. Research). The amplification cycle is repeated up to about 40 times with denaturation and extension taking place at about 94° C. for about 1 min and 72° C. for about 2 min, respectively. The annealing temperature will depend on the primers used.

VII. PRIMERS AND PROBES

Primers for the reverse transcription and amplification steps of the present invention are chosen to efficiently amplify nucleic acid sequences from organisms within a particular genus of protozoa, e.g. Cryptosporidium or Giardia. Alternatively, primers are chosen which only amplify a single protozoan species within a genus, e.g the human pathogens *C. parvum* or *G. lamblia*. The targets for amplification, i.e., the HSP sequences, are genes which can be easily induced to produce mRNA, since organisms capable of transcribing mRNA are viable and potentially infectious. If a Cryptosporidium oocyst or Giardia cyst is not viable then it will not produce HSP mRNA.

Primers and probes are preferably synthetic oligonucleotides, which can be prepared by an automated instrument (e.g, Applied Biosystems Inc., Foster City, Calif.). Alternatively, customized oligonucleotide primer and probes can be purchased from commercial suppliers, e.g., National Biosciences, Inc., Plymouth, Minn.

Preferred primer pairs and probes target the HSP70 gene sequence of *C. parvum* (SEQ ID NO: 1, see also, Khramtsov et al., 1995). An alignment of HSP70 gene sequences from a range of organisms was done to find primers and probes for Cryptosporidium, which have an average sequence similarity of only 60% with mammalian HSP70 genes. Therefore, false positives due to non-specific amplification of host cell HSP70 genes are not a problem. Furthermore, DNA extracted from uninfected mammalian cells does not yield amplification products with these primers.

A most preferred primer pair (SEQ ID NO: 2 and SEQ ID NO: 3) can amplify DNA or RNA from many different Cryptosporidium species. Another most preferred primer pair (SEQ ID NO: 4 and SEQ ID NO: 5) is specific to *C. parvum*. Each set of primers has an internal oligonucleotide probe, which can be used to confirm the identity of the amplification product.

A. CRYPTOSPORIDIUM PRIMERS

Figure 1:
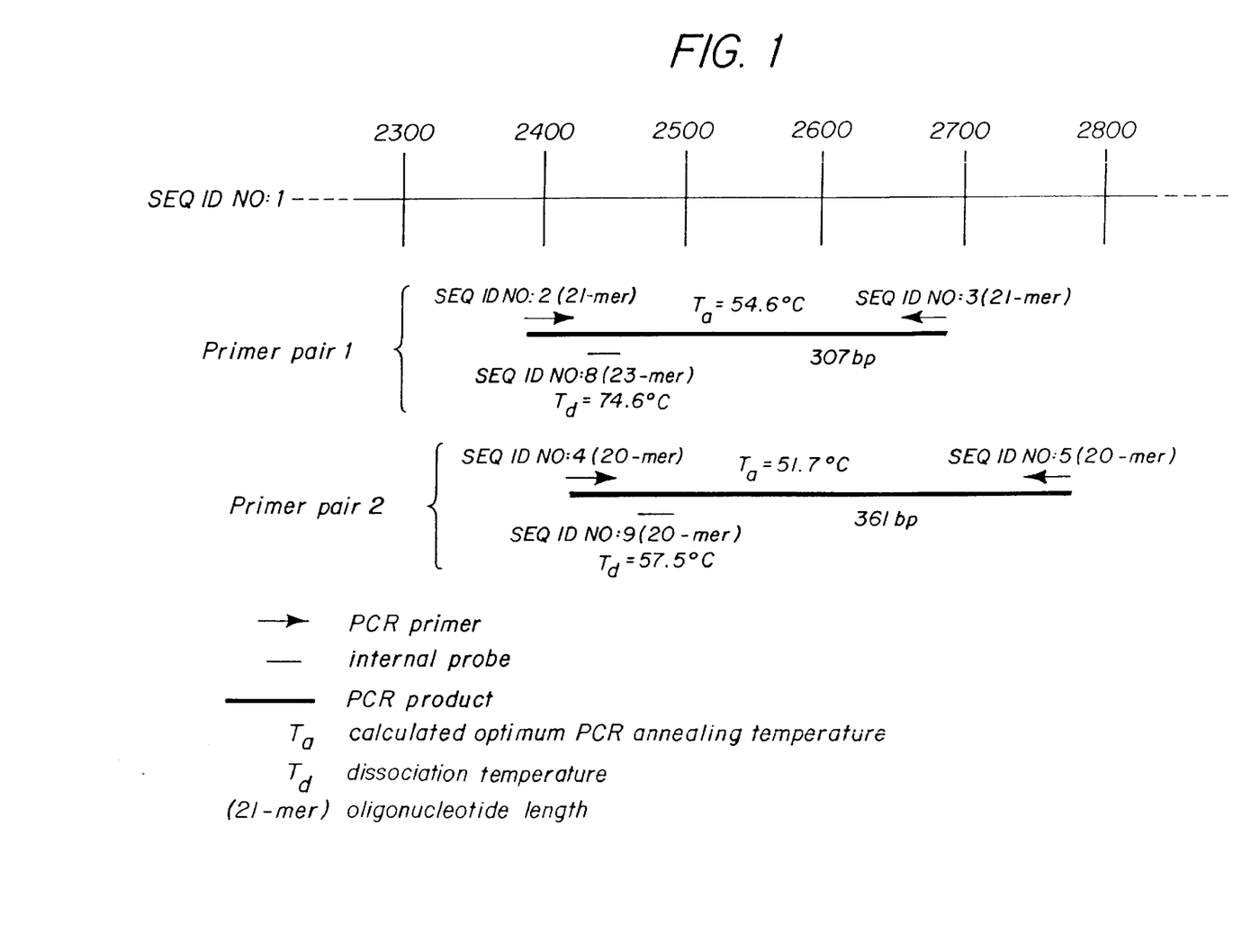
FIG. 1 is a diagram showing the relative map positions of primer pair SEQ ID NO: 2 and SEQ ID NO: 3, primer pair SEQ ID NO: 4 and SEQ ID NO: 5, probe SEQ ID NO: 8, and probe SEQ ID NO: 9 within the HSP70 gene sequence SEQ ID NO: 1.

In one embodiment, primer pairs can amplify DNA or RNA from several Cryptosporidium species. A most preferred primer pair is:
SEQ ID NO: 2: CTG TTG CTT ATG GTG CTG CTG, and
SEQ ID NO: 3: CCT CTT GGT GCT GGT GGA ATA,
which typically gives a 307 base pair amplification product from Cryptosporidium nucleic acid extracts (see FIG. 1). The experimentally determined optimum annealing temperature of SEQ ID NO: 2 and SEQ ID NO: 3 is about 55° C.

In a second embodiment, the primer pairs are specific for *C. parvum*. The second embodiment is exemplified by the following most preferred primer pair:
SEQ ID NO: 4: AAA TGG TGA GCA ATC CTC TG, and
SEQ ID NO: 5: CTT GCT GCT CTT ACC AGT AC,
which typically gives a 361 base pair amplification product from *C. parvum* nucleic acid extracts (see FIG. 1). The experimentally determined optimum annealing temperature of SEQ ID NO: 4 and SEQ ID NO: 5 is about 55° C.

B. MULTIPLEX PRIMERS

In a third embodiment, primer pairs specific for Giardia are combined with Cryptosporidium specific pairs for a "multiplex" amplification. For example, the DNA sequence for a heat shock protein in *G. lamblia* that is unrelated to HSP 70, has been described (Aggarwal et al., 1990, incorporated herein by reference). Moreover, primers targeting the HSP gene have been described, which are suitable for the detection of viable *G. lamblia* cysts in water samples (Abbaszadegan et al., 1993, incorporated herein by reference) The following primers:
SEQ ID NO: 6: AGGGCTCCGGCATAACTTTCC, and
SEQ ID NO: 7: GTATCTGTGACCCGTCCGAG,
amplify a 163 base pair product from *G. lamblia*. The optimum annealing temperature for SEQ ID NO: 6 and SEQ ID NO: 7 is about 55° C. and the optimum MgCl$_2$ concentration is 2.5 mM.

When *G. lamblia* specific primers, and *C. parvum* specific primers are combined in a single amplification reaction mixture, two amplification products are produced. For example, the primer pair SEQ ID NO: 6 and SEQ ID NO: 7 and primer pair SEQ ID NO: 4 and SEQ ID NO: 5 can be used to amplify two separate HSP sequences at an annealing temperature of about 52° C. (see FIG. 2B lane 4). The first amplification product is a 361 base pair DNA fragment, corresponding to *C. parvum* HSP 70 sequences. The second amplification product is a 163 base pair DNA fragment, corresponding to sequences of a *G. lamblia* heat shock protein gene that are unrelated to HSP 70.

VIII. DETECTION

The amplified HSP target DNA can be detected directly by any method that can distinguish among different lengths of DNA. Electrophoresis through agarose is the standard method used to separate, identify, and purify DNA fragments. The location of DNA within the gel can be determined directly by staining with low concentrations of the fluorescent intercalating dye ethidium bromide. Bands corresponding to the predicted length for amplified target DNA can then be detected by direct examination of the gel in ultraviolet light.

In addition, the DNA bands from an electrophoresed gel can be transferred to a membrane support by capillary action, followed by indirect detection using oligonucleotide probes. A typical transfer protocol includes denaturing the DNA within the gel using an alkaline solution, such as 0.4M NaOH, 0.6M NaCl, followed by a neutralization step in a buffer solution, e.g. 1.5M NaCl, 0.5M Tris-HCl, pH 7.5. The gel is then equilibrated with a high ionic strength transfer buffer, such as 1 OX SSC, wherein 1X SSC is 0.15M NaCl, 0.015M Na citrate. The denatured DNA can then be transferred from the gel to a membrane support by capillary blotting in transfer buffer.

A. HYBRIDIZATION PROBES

A preferred mode for detecting amplified target sequences is via hybridization to a single-stranded oligonucleotide probe which is sequence-complementary to a sequence located between the two selected oligonucleotide primers in the target HSP gene. The identity of the amplified extension products from each set of primers can thereby be confirmed using the sequence specific probes. Oligonucleotide probes are normally selected according to their ability to hybridize with an internal sequence of an amplified target DNA. Thus, probes that can detect the amplified products of the viability or infectivity assays are complementary to an amplified heat shock protein gene sequence, preferably HSP70.

A most preferred probe is an oligonucleotide, which specifically hybridizes with HSP70 sequences of *C. parvum*. The following two probes are exemplary of *C. parvum* specific probes:
SEQ ID NO: 8: AAA TGG TGA GCA ATC CTC TGC CG
SEQ ID NO: 9: CCA TTA TCA CTC GGT TTA GA The first *C. parvum* HSP70 specific probe, SEQ ID NO: 8, contains sequences corresponding to nucleotide base numbers 2423 to 2446 of SEQ ID NO: 1. The SEQ ID NO: 8 probe can be used to detect *C. parvum* specific sequences of any HSP70 targets having complementary sequences to nucleotide base numbers 2423 to 2446 of SEQ ID NO: 1. Consequently, SEQ ID NO: 8 can be used to detect the amplification products of the SEQ ID NO: 2 and SEQ ID NO: 3 primer pair (see FIG. 1).

The second *C. parvum* HSP70 specific probe, SEQ ID NO: 9, contains sequences corresponding to nucleotide base numbers 2475 to 2495 of SEQ ID NO: 1. The SEQ ID NO: 9 probe can be used to detected *C. parvum* specific sequences of any HSP70 targets having complementary sequences to nucleotide base numbers 2475 to 2495 of SEQ ID NO: 1. Accordingly, SEQ ID NO: 9 can be used to detect the amplification products of a variety of primer pairs, such as SEQ ID NO: 2 and SEQ ID NO: 3; SEQ ID NO: 2 and SEQ ID NO: 5; and SEQ ID NO: 4 and SEQ ID NO: 5 (see FIG. 1).

Similarly, when primers pairs, such as SEQ ID NO: 6 and SEQ ID NO: 7, are used to amplify G. lamblia specific sequences, an internal probe can be used to confirm the identity of the Giardia targets. For example, the following internal oligonucleotide probe can be used for detecting G. lamblia HSP targets.

SEQ ID NO: 10: CAGGCCTTGGCGTTCCCGAAG.

Giardia HSP probes are especially useful in a "multiplex" amplification procedure, which includes primers for both Giardia and Cryptosporidium target sequences. The Giardia HSP probes can then be used to distinguish Giardia specific amplification products from any other amplification products.

B. HYBRIDIZATION OF SOUTHERN BLOTS

Amplified target DNA that has been captured on a solid support, such as nylon or nitrocellulose membrane, can be detected by using a labeled hybridization probe. The probe can be labeled with a radioactive or fluorescent tag, or attached directly or indirectly to an enzyme molecule. Then, the membrane-bound amplified target DNA is incubated with the probe under hybridization conditions. Following hybridization, excess probe is washed away. If the hybridization probe is radioactively tagged, the remaining hybridized probe can be detected by autoradiography or scintillation counting. If the probe contains biotin or some other chemical group for which there are specific binding molecules, like avidin and antibodies, then the immobilized probe can be detected with an enzyme attached to the specific binding molecule, such as horseradish peroxidase or alkaline phosphatase attached to streptavidin.

A preferred method of detection is via hybridization with a nonradioactive 5'digoxigenin (DIG)-labeled oligonucleotide probe. Following hybridization the solid support is washed with a high ionic strength buffer, such as 5X SSC, at about 70° C. The immobilized hybridization probe that remains after washing can be visualized by incubating the solid support with anti-DIG antibody conjugated to alkaline phosphatase, followed by addition of a chemiluminescent substrate, such as Lumigen-PPD (Boehringer Mannheim). The support is finally washed, sealed in Saran Wrap, and exposed to X-ray film to detect any chemiluminescence.

C. IN SITU DETECTION

There are two approaches for the detection of in situ amplification products. The first in situ detection method is a direct technique, which involves incorporation of a label directly into the amplification product. For example, a reporter molecule such as digoxigenin [DIG]-dUTP or fluorescein-dUTP can be included in the amplification cocktail and incorporated into the amplification product. A simple immunochemical step using alkaline phosphatase- or peroxidase-conjugated anti-DIG then detects DIG labeled amplification products. Alternatively, fluorescein labeled amplification products can be detected by fluorescence microscopy or immunochemical methods.

The second in situ detection method is an indirect technique, which involves hybridization of a specific labeled probe to the amplification product after PCR. The label on the probe is then detected either by immunochemical methods or fluorescence microscopy. The indirect method is preferred because it has a higher specificity than direct in situ PCR. Moreover, by using multiple probes for in situ hybridization, each labeled with a different fluorescent molecule, e.g., fluorescein, rhodamine, and couramin, each targeting different amplification products, the potential exists for detecting multiple target genes in a single sample.

By combining reverse transcription of RNA and in situ amplification with cell culture infectivity assays a method has been developed which allows the sensitive and specific detection of expressed Cryptosporidium and Giardia genes. Expression of the target genes indicates the presence of viable protozoa within cell cultures grown on microscope slides. In addition, such a method determines the infectivity potential of Cryptosporidium oocysts and Giardia cysts within about 48 to about 72 hours after inoculation.

IX. KITS

The primers and/or probes, used to amplify and detect viable or infective Cryptosporidium and/or Giardia organisms, can be conveniently packaged as kits. The kit may comprise suitable amounts of the primers, or a suitable amount of the probe, or suitable amounts of the primers and probe. In addition, kits can contain a suitable amount of at least one standard sample, which contains a known concentration of a Cryptosporidium or Giardia species, and a negative control sample substantially free of the protozoa of interest.

The methods and kits of the present invention have many advantages over previous methods, including the speed, sensitivity, and specificity associated with amplification procedures, such as PCR. Since the methods can detect only viable and infectious forms of Cryptosporidium and Giardia, the effectiveness of disinfection procedures can be monitored. Moreover, the human pathogen, C. parvum, can be distinguished from other Cryptosporidia, such as C. muris and C. baileyi, which only infect animal hosts.

EXAMPLES

Materials & Methods

Purified preparations of C. parvum oocysts and G. lamblia cysts were obtained from two commercial laboratories Parasitology Research Laboratories (PRL), Phoenix, Ariz. and Waterborne, Inc., New Orleans, La. C. muris oocysts were generous gifts of J. Owens (United States Environmental Protection Agency, Cincinnati, Ohio) and are available commercially from PRL. C. baileyi oocysts were generous gifts of Dr. B. Blagburn (Auburn University, Auburn, Ala.) Cysts and oocysts were supplied as purified preparations stored in antibiotic solution or as unpurified concentrates and were stored at 4° C. Cyst and oocyst densities were determined by hemocytometer counting and lower densities were obtained by serial dilution of concentrated stocks.

Example 1

Specificity of primer pairs for C. parvum and C. muris oocyst DNA

This example compares the specificity of primers directed to different portions of the HSP70 gene, an undefined genomic region of Cryptosporidium DNA, and the 18 S rRNA gene, for C. parvum and C. muris.

DNA was extracted from C. parvum and C. muris oocysts by freezing in liquid nitrogen for 2 min, followed by thawing at 95° C. for 5 min. Five $\mu$l of the freeze-thaw lysate (equivalent to about 1,000 cysts or oocysts) was added to individual amplification reactions, which also contained: 10 mM Tris-HCl, pH 8.3; 50 mM KCl; 0.01% gelatin; 2.5 mM MgCl$_2$, 0.25 $\mu$M of each primer, 200 $\mu$M each of dATP, dCTP, dGTP and dUTP; and 2 U of Amplitaq® DNA polymerase (Perkin-Elmer, Foster City, Calif.) in a 100-$\mu$L volume.

The reactions were overlaid with two drops of sterile mineral oil (Sigma Chemical Co., St. Louis, Mo.). Hot start reactions were performed in a DNA Thermal Cycler model 480 (Perkin-Elmer) with denaturation at 94° C. for 2 min, followed by 40 cycles of denaturation at 94° C. for 1 min, annealing for 1 min at 50° C. and extension at 72° C. for 1 min. A final extension incubation at 72° C. for 5 min was included followed by 5 min at 5° C. to stop the reactions.

Figure 2A:
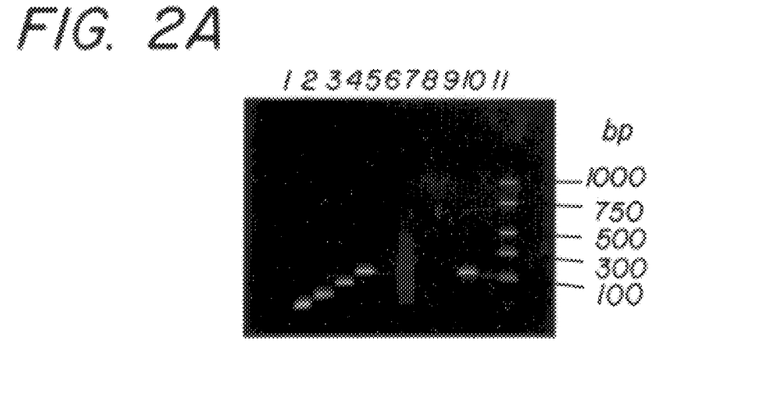
FIG. 2B shows amplification of DNA from C. parvum and G. lamblia using primer pair SEQ ID NO: 2 and SEQ ID NO: 3 to give a 307 bp Cryptosporidium specific product (lane 1), primer pair SEQ ID NO: 4 and SEQ ID NO: 5 to give a Cryptosporidium specific 361 bp (lane 2), primers SEQ ID NO: 2 and SEQ ID NO: 3 combined with SEQ ID NO: 6 and SEQ ID NO: 7 for a multiplex PCR (lane 3), primers SEQ ID NO: 4 and SEQ ID NO: 5 combined with SEQ ID NO: 6 and SEQ ID NO: 7, which target heat shock protein genes of C. parvum (361 bp product) and G. lamblia (163 bp product), respectively (lane 4); negative controls (lanes 5 and 6); and digoxigenin-labeled molecular weight markers (lane 7)
FIG. 2C shows a Southern blot of the gel shown in FIG. 3B hybridized with an internal oligonucleotide probe specific for both of the C. parvum amplification products (307 bp and 361 bp), which was labeled with fluorescein and detected by a chemiluminescent reaction mediated by alkaline phosphatase conjugated anti-fluorescein antibody.

PCR products (15% of the amplification reaction) were detected by standard agarose gel electrophoresis and ethidium bromide staining as shown in FIG. 2A. Primer pair SEQ ID NO: 2 and SEQ ID NO: 3, which is directed to a portion of the HSP70 gene, primed the amplification of a 307 base pair (bp) product from both C. parvum and C. muris DNA extracts (see Lanes 1 and 6 of FIG. 2A). In contrast, primer pair SEQ ID NO: 4 and SEQ ID NO: 5, which is directed to a different portion of HSP70 gene, primed the amplification of a 361 bp product from C. parvum, but not C. muris DNA extracts (see Lanes 2 and 7 of FIG. 2A).

These results compare favorably with primer pairs directed to the 18S rRNA gene (Awad-El-Kariem et al., 1994), which primed the synthesis of amplification products from C. parvum and C. muris extracts (see FIG. 2A, lanes 4, 5, 9, and 10). In addition, primers directed to an unspecified genomic region of Cryptosporidium DNA (Laxer et al., 1991) primed a 451 base pair amplification product from C. parvum extracts (see FIG. 2A, lane 3).

Thus, primer pair SEQ ID NO: 2 and SEQ ID NO: 3 exemplifies an HSP 70 primer pair that is specific for at least two different members of the Cryptosporidium genus, whereas the specificity of primer pair SEQ ID NO: 4 and SEQ ID NO: 5 was limited to C. parvum.

Example 2

Multiplex primer amplification of C. parvum and G. lamblia followed by C. parvum oligoprobe detection This example illustrates that a combination of two primer pairs directed to C. parvum and G. lamblia HSP sequences can accurately amplify both target sequences simultaneously. Moreover, the identity of the C. parvum amplification product can be confirmed using a C. parvum specific oligonucleotide probe.

DNA was extracted from C. parvum oocysts and G. lamblia cysts by freezing in liquid nitrogen for 2 min, followed by thawing at 95° C. for 5 min. The amplification reaction contained 10 mM Tris-HCl, pH 8.3; 50 mM KCl; 0.01% gelatin; 1.5 mM $MgCl_2$; 0.25 µM of each primer; 200 µM each of dATP, dCTP, dGTP and dUTP; and 2 U of Amplitaq® DNA polymerase (Perkin-Elmer, Foster City, Calif.) in a 100-µL volume with 5 µL template DNA. Negative control reactions contained sterile distilled water in place of template DNA.

The reactions were overlaid with two drops of sterile mineral oil (Sigma Chemical Co., St. Louis, Mo.). Hot start reactions were performed in a DNA Thermal Cycler model 480 (Perkin-Elmer) with denaturation at 94° C. for 2 min, followed by 40 cycles of denaturation at 94° C. for 1 min, annealing for 1 min at 52° C., and extension at 72° C. for 1 min. A final extension incubation at 72° C. for 5 min was included, followed by 5 min at 5° C. to stop the reactions.

Figure 2B:
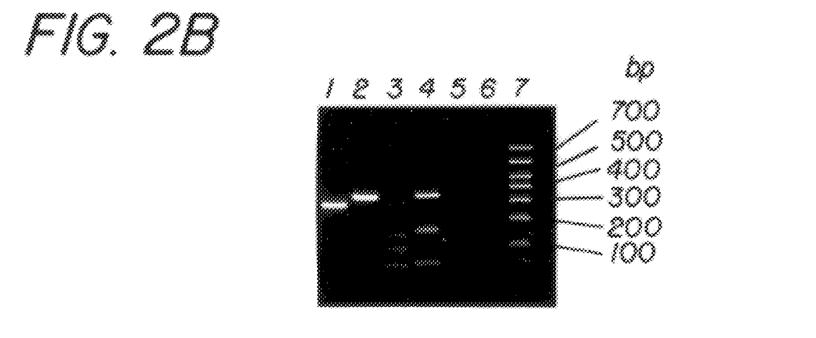

PCR products (15% of the amplification reaction) were detected by standard agarose gel electrophoresis and ethidium bromide staining (see FIG. 2B). Reactions primed only with SEQ ID NO: 2 and SEQ ID NO: 3 exhibited the expected 307 base pair product (FIG. 2B, lane 2). Similarly, reactions primed only with SEQ ID NO: 4 and SEQ ID NO: 5 exhibited the expected 361 base pair product (FIG. 2B, lane 1). Amplification products from reactions primed with both primer pair SEQ ID NO: 2 and SEQ ID NO: 3, and primer pair SEQ ID NO: 6 and SEQ ID NO: 7 were not visible on the ethidium bromide stained gel (see FIG. 2B, lane 3). However, two amplification products, 361 base pairs and 163 base pairs in length, were detected from reactions primed with SEQ ID NO: 4 and SEQ ID NO: 5, and primer pair SEQ ID NO: 6 and SEQ ID NO: 7 (see FIG. 2B, lane 4). The 361 base pair and 163 base pair bands correspond with the expected size of the amplification products for C. parvum and G. lamblia, respectively.

DNA was denatured by incubation of the gel for 30 min each in 0.4M NaOH, 0.6M NaCl followed by 1.5M NaCl, 0.5M Tris-HCl, pH 7.5 at room temperature. The gel was then incubated for 20 min in 10 x SSC (1X SSC is 0.15M NaCl, 0.015M Na citrate). Denatured DNA was transferred to a positively charged nylon membrane (Boehringer Mannheim) by overnight capillary blotting in 10 X SSC. Transferred DNA was cross-linked to the membrane by UV irradiation (120 mJ for 2 min) followed by drying at 80° C.

The membrane was prehybridized for 1 h in 20 of hybridization solution which contained 5X SSC, 1 % blocking reagent (Boehringer Mannheim), 0.1 % sarcosine, 0.02% SDS at 64° C. The membrane was then hybridized in fresh hybridization solution containing 50 pmoles of 5'-fluorescein labeled oligonucleotide probe SEQ ID NO: 9 for 18 h at 64° C. in a rotary hybridization oven (Model 310, Robbins Scientific, Sunnyvale, Calif.). Stringency washes containing 20 mM Tris-HCl, pH 7.4, 0.01% SDS, and 5X SSC were performed at 70° C., twice for 15 min each.

Hybridized probe was detected with an anti-fluorescein alkaline phosphatase conjugate and a chemiluminescent substrate. Membranes were washed for 5 min in 20 ml of 0.3% Tween 20 followed by 30 min incubation in 100 ml of 1 % blocking reagent. Both of these solutions were made up in 0.1M maleic acid, 0.15M NaCl, pH 7.5 and all incubations were at 23° C. in a rotary hybridization oven. Fluorescein labeled anti-Digoxigenin (1.5 U, Boehringer Mannheim) was added in 20 ml of 0.1M Tris-HCl, pH 7.5, 0.15M NaCl, 1% blocking reagent and incubated for 15 min to label the molecular size markers. Anti-fluorescein alkaline phosphatase (1.5 U, Boehringer Mannheim) was added to the membrane in 20 ml of 0.1M Tris-HCl, pH 7.5, 0.15M NaCl, 1% blocking reagent and incubated for 30 min. The membranes were washed twice in 100 ml of 0.3% Tween 20 followed by 5 min in 20 ml of 0.1M Tris, 0.1M NaCl, 50 mM $MgCl_2$, pH 9.5 and then incubated for 15 min at 37° C. with Lumigen®-PPD (0.1 mg/ml; Boehringer Mannheim) in 1 ml of 0.1M Tris, 0.1M NaCl, 50 mM $MgCl_2$, pH 9.5.

Figure 2C:
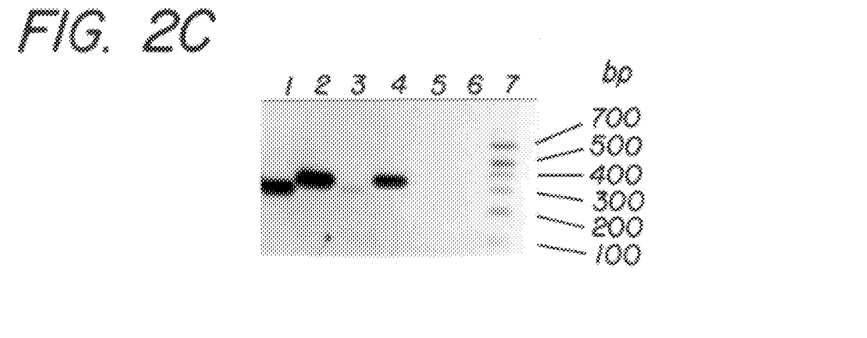

The membrane was sealed in Saran Wrap and incubated at room temperature for 1 hour prior to exposure to X-ray film (Fuji RX, Fisher Scientific, Tustin, Calif.) for 15 min. The developed film (FIG. 2C) shows that the SEQ ID NO: 9 probe specifically detected C. parvum amplification products that are 307 base pair (FIG. 2C, lanes 1 and 3) and 361 base pair (FIG. 2C, lanes 2 and 4) in size. Moreover, the C. parvum specific probe did not hybridize with G. lamblia sequences from either multiplex reaction (FIG. 2C, lanes 3 and 4)

Example 3

Differential amplification and detection of Cryptosporidium DNA from oocysts

This example illustrates the use of Cryptosporidium genus specific primers to amplify DNA extracted from a variety of Cryptosporidium species. In addition, this example demonstrates the use of a Cryptosporidium species specific primer pair to selectively amplify C. parvum HSP70 DNA. Moreover, the example demonstrates differential detection of C. parvum amplification products using a species specific probe.

DNA was extracted from *C. parvum*, *C. muris* and *C. baileyi* oocysts by freezing in liquid nitrogen for 2 min, followed by thawing at 95° C. for 5 min. Amplification reactions were conducted using primer pair SEQ ID NO: 2 and SEQ ID NO: 3 (see FIG. 3A, lanes 4 to 6) or primer pair SEQ ID NO: 4 and SEQ ID NO: 5 (see FIG. 3A, lanes 1 to 3) essentially as described in Example 1. The PCR products (15% of the amplification reaction) were detected by standard agarose gel electrophoresis and ethidium bromide staining, as shown in FIG. 3A.

Figure 3A:
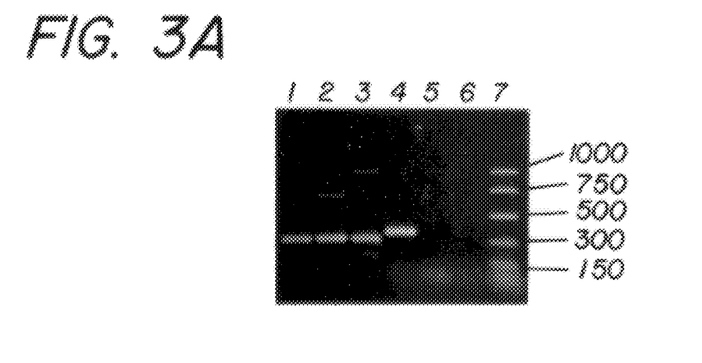
FIG. 3A shows amplification, with primers SEQ ID NO: 2 and SEQ ID NO: 3 (lanes 1–3) and primers SEQ ID NO: 4 and SEQ ID NO: 5 (lanes 4–6), of DNA fragments from the following Cryptosporidium species.: C. parvum (lanes 1 and 4); C. muris (lanes 2 and 5); C. baileyi (lanes 3 and 6); Lane 7 shows 50, 150, 300, 500, 750, 1000-bp molecular size standards.

Primer pair SEQ ID NO: 2 and SEQ ID NO: 3 amplified nucleic acid sequences from *C. parvum* (FIG. 3A, lane 1), *C. muris* (FIG. 3A, lane 2), and *C. baileyi* (FIG. 3A, lane 3). In contrast, primer pair SEQ ID NO: 4 and SEQ ID NO: 5 only amplified DNA target sequences from *C. parvum* (FIG. 3A, lane 4).

Figure 3B:
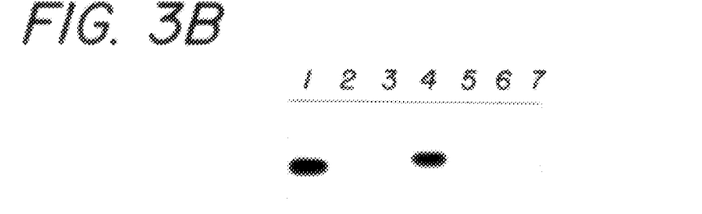
FIG. 3B shows a Southern blot of the gel shown in FIG. 3A hybridized with the SEQ ID NO: 9 oligonucleotide probe, which was labeled with fluorescein and detected by chemiluminescence using an anti-fluorescein antibody conjugated to alkaline phosphatase.

A Southern blot of the gel shown in FIG. 3A was performed as described in Example 2. Moreover, hybridization with probe SEQ ID NO: 9, washing, and probe detection were also done essentially as described in Example 2. The *C. parvum* specific probe did not hybridize with the *C. muris* (FIG. 3B, lane 2), and *C. baileyi* (FIG. 3B, lane 3) amplification products, but did detect both *C. parvum* HSP70 amplification products (FIG. 3B, lanes 1 and 4).

Example 4

Amplification using extracts from infected cell cultures and seeded environmental water concentrates This example illustrates methods for recovering and concentrating oocysts from water samples, In addition, the example illustrates an effective method for extracting template DNA from infected cells and oocysts for use in amplification reactions.

641 L of source water (0.65 NTU) was filtered through a 1 μm nominal porosity yarn-wound polypropylene filter. The filtration flow rate was restricted to about 4 liters/min. The filter fibers were then cut, teased and washed with a buffered detergent solution. Any oocysts or cysts that may have been eluted from the filter were concentrated by centrifugation and partially purified by flotation on a Percoll-sucrose solution with a specific gravity of 1.1. The final volume of the concentrated oocyst or cyst containing fraction was 1.3 ml. A 100 μl amount of this concentrate was seeded with 0.5–500 *C. parvum* oocysts (determined by serial dilution).

Total DNA was extracted from infected mammalian cell cultures and seeded concentrates of source water samples (100 μl) by lysis in 50 mM Tris-HCl, 20 mM EDTA, pH 8, containing 2 mg/proteinase K and 0.5% sarkosyl, followed by incubation at 37° C. for 1 h. Then, 5M NaCl was added to give a final concentration of 1M, and CTAB was added to a concentration of 1 %. Following incubation at 65° C. for 30 min, the lysate was subjected to one freeze/thaw cycle and phenol/chloroform extraction. The DNA was precipitated by the addition of 0.6 vol of isopropanol, and the DNA precipitate was washed with 70% ethanol. After desiccation, the DNA pellet was resuspended in 100 μL of sterile distilled water.

The amplification reaction conditions using primer pair SEQ ID NO:4 and SEQ ID NO: 5 were generally the same as in Example 1. DNA was amplified by 40 cycles of denaturation at 94° C. for 45 sec, annealing for 45 sec at 55° C. and extension at 72° C. for 1 min in reactions containing 1.5 mM MgCl$_2$. The seeded water concentrate amplification reactions also contained 10 μg/ml BSA.

Figure 3C:
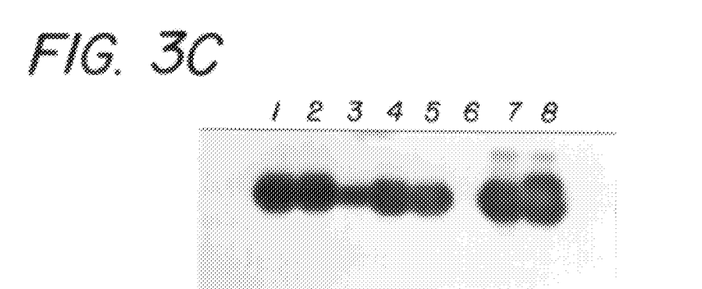
FIG. 3C shows hybridization of the SEQ ID NO: 9 probe with the C. parvum specific PCR products of primers SEQ ID NO: 4 and SEQ ID NO: 5 using DNA extracted from 5 individual growth chambers containing mammalian cell cultures infected with C. parvum (lanes 1–5), uninfected cultured cells (lane 6), and environmental water concentrates seeded with C. parvum (lanes 7 and 8).

PCR products (15% of the amplification reaction) were detected by standard agarose gel electrophoresis and ethidium bromide staining. DNA transfer, hybridization and detection were performed essentially as described in Example 2. The membrane was hybridized with the SEQ ID NO: 9 probe in 1 x SSC at 57° C. for 18 h and washed in 1 x SSC at 54° C. The developed film (FIG. 3C) shows that the primer and probe combination gave a strong detection signal whenever *C. parvum* specific sequences were present in the DNA extracts (lanes 1–5, infected mammalian cell cultures, and lanes 6–7, environmental water concentrates seeded with *C. parvum*).

Although the present invention has been described in considerable detail with reference to certain preferred versions thereof, other versions are possible. For example, primers and probes can have additional nucleotide sequences that function as recognition sites for DNA-binding proteins. Therefore, the spirit and scope of the appended claims should not be limited to the description of the preferred versions described herein.

What is claimed is:

1. A method of selectively detecting viable, infectious *Cryptosporidium parvum* organisms in a sample potentially containing viable, infectious *Cryptosporidium parvum* organisms and other Cryptosporidium organisms, the method com heat shock protein for *Giardia lamblia* from a second primer which produces polynucleotide from a portion of the heat shock protein RNA for *Giardia lamblia;*

(c) exposing any *Cryptosporidium parvum* HSP 70 polynucleotide produced in step (b) to conditions suitable to produce double-stranded *Cryptosporidium parvum* HSP 70 polynucleotide but not suitable to produce polynucleotide from a portion of HSP 70 of other Cryptosporidium species, and exposing any *Giardia lamblia* heat shock protein polynucleotide produced in step (b) to conditions suitable to produce double-stranded heat shock protein polynucleotide for *Giardia lamblia;*

(d) exposing any double-stranded *Cryptosporidium parvum* HSP 70 polynucleotide and any double-stranded heat shock protein polynucleotide for *Giardia lamblia* produced in step (c) to conditions suitable to amplify the double-stranded polynucleotide formed in step (c); and (e) detecting the presence of any amplified double-stranded *Cryptosporidium parvum* HSP 70 polynucleotide and any amplified heat shock protein polynucleotide for *Giardia lamblia* polynucleotide formed in step (d);

wherein the presence of amplified double-stranded *Cryptosporidium parvum* HSP 70 polynucleotide detected in step (e) indicates the presence of viable, infectious *Cryptosporidium parvum* organisms in the sample; and wherein the presence of amplified double-stranded heat shock protein polynucleotide for *Giardia lamblia* polynucleotide detected in step (e) indicates the presence of viable, infectious *Giardia lamblia* organisms in the sample.

6. The method of claim 5, wherein the portion of *Cryptosporidium parvum* HSP 70 is that portion of SEQ ID NO: 1 extending from about nucleotide 2386 to about 2784.

7. The method of claim 5, wherein the first primer is selected from the group consisting of SEQ ID NO:4 and SEQ ID NO:5.

8. The method of claim 5, wherein the second primer is selected from the group consisting of SEQ ID NO:6 and SEQ ID NO:7.

9. The method of claim 5, wherein the detecting step is performed by subjecting the amplified polynucleotide to hybridization conditions with at least one probe selected from the group consisting of SEQ ID NO:8, SEQ ID NO:9, SEQ ID NO:10, the complement of SEQ ID NO:8, the complement of SEQ ID NO:9 and the complement of SEQ ID NO: 10.

10. A method of selectively detecting viable, infectious *Cryptosporidium parvum* organisms in a sample potentially containing viable, infectious *Cryptosporidium parvum* organisms and other Cryptosporidium species organisms, the method comprising the steps of:

(a) inoculating a cell culture with the sample potentially containing viable, infectious *Cryptosporidium parvum* organisms, wherein the cell culture is susceptible to infection by viable, infectious *Cryptosporidium parvum* organisms;

(b) incubating the cell culture under conditions suitable for any viable, infectious *Cryptosporidium parvum* organisms present in the sample to infect the cell culture and to cause any infectious *Cryptosporidium parvum* organisms present in the sample to produce *Cryptosporidium parvum* HSP 70 RNA;

(c) selectively producing *Cryptosporidium parvum* HSP 70 polynucleotide from the Cryptosporidium parvum HSP 70 RNA utilizing a primer which produces polynucleotide from a portion of *Cryptosporidium parvum* HSP 70 RNA but which does not produce polynucleotide from a portion of HSP 70 of other Cryptosporidium species;

(d) exposing any *Cryptosporidium parvum* HSP 70 cDNA produced in step (c) to conditions suitable to produce double-stranded DNA from the *Cryptosporidium parvum* HSP 70 polynucleotide;

(e) exposing any *Cryptosporidium parvum* HSP 70 polynucleotide produced in step (d) to conditions suitable to amplify any double-stranded polynucleotide formed in step (d); and (f) detecting the presence of any amplified polynucleotide formed in step (e);

wherein the presence of amplified polynucleotide detected in step (f) indicates the presence of viable, infectious *Cryptosporidium parvum* organisms in the sample.

11. The method of claim 10, wherein the cell culture comprises a number of cells, the sample comprises a number of viable, infective oocysts, and wherein the number of cells exceeds the number of viable, infective oocysts.

12. The method of claims 1, 5 or 10, wherein the amplification is accomplished by the polymerase chain reaction.

13. The method of claim 10, wherein the primer is selected from the group consisting of SEQ ID NO:4 and SEQ ID NO:5.

14. The method of claim 10, wherein the portion of *Cryptosporidium parvum* HSP 70 is that portion of SEQ ID NO: 1 extending from about nucleotide 2386 to about 2784.

15. The method of claim 10, wherein the detecting step is performed by subjecting the amplified polynucleotide to hybridization conditions with a probe selected from the group consisting of SEQ ID NO:8, SEQ ID NO:9, the complement of SEQ ID NO:8 and the complement of SEQ ID NO: 9.

16. A kit for detecting *Cryptosporidium parvum,* the kit comprising a first primer and a second primer for amplification of a portion of *Cryptosporidium parvum* HSP 70 MRNA that is specific for *Cryptosporidium parvum.*

17. The kit of claim 16, further comprising a probe for detection of the amplified portion of *Cryptosporidium parvum* HSP 70 polynucleotide.

18. The kit of claim 16, wherein the first primer or the second primer is selected from the group consisting of SEQ ID NO:4 and SEQ ID NO:5.

19. The kit of claim 17, wherein the probe is selected from the group consisting of SEQ ID NO:8, SEQ ID NO:9, the complement of SEQ ID NO:8 and the complement of SEQ ID NO:9.

20. A kit for detecting *Cryptosporidium parvum* and *Giardia lamblia,* the kit comprising a first primer and a second primer for amplification of a portion of *Cryptosporidium parvum* HSP 70 mRNA that is specific *Cryptospo-*

*ridium parvum* and a third primer and a fourth primer for amplification of a target sequence of *Giardia lamblia*.

21. The kit of claim 20, further comprising a probe for detection of the amplified portion of *Cryptosporidium parvum* HSP 70 polynucleotide.

22. The kit of claim 20, further comprising a probe for detection of the amplified portion of the target sequence that is specific to *Giardia lamblia*.

23. The kit of claim 22, wherein the probe is selected from the group consisting of SEQ ID NO:8, SEQ ID NO:9, the complement of SEQ ID NO:8 and the complement of SEQ ID NO:9.

24. The kit of claim 20, wherein the first primer or the second primer is selected from the group consisting of SEQ ID NO:4 and SEQ ID NO:5.

25. The kit of claim 24, wherein the probe is selected from the group consisting of SEQ ID NO:10 and the complement of SEQ ID NO: 10.

26. The kit of claim 20, wherein the third primer or the fourth primer is selected from the group consisting of SEQ ID NO:6 and SEQ ID NO:7.

* * * * *